(12) United States Patent
Chang et al.

(10) Patent No.: US 6,217,859 B1
(45) Date of Patent: Apr. 17, 2001

(54) MICROENCAPSULATED GENETICALLY ENGINEERED MICROORGANISMS FOR CLINICAL APPLICATION

(75) Inventors: Thomas M. S. Chang, St-Lambert; Satya Prakash, Montréal, both of (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/117,099

(22) PCT Filed: Jul. 20, 1997

(86) PCT No.: PCT/CA97/00040
§ 371 Date: Jul. 22, 1998
§ 102(e) Date: Jul. 22, 1998

(87) PCT Pub. No.: WO97/26903
PCT Pub. Date: Jul. 31, 1997

(30) Foreign Application Priority Data

Jan. 23, 1996 (GB) .................................... 9601333

(51) Int. Cl.[7] .................................................. A01N 63/00

(52) U.S. Cl. .................. 424/93.2; 424/94.6; 424/439; 424/484; 424/494; 424/487; 424/490; 514/44

(58) Field of Search .................... 264/5–14; 424/450, 424/451, 490; 435/177

(56) References Cited

U.S. PATENT DOCUMENTS

| 4,391,909 | 7/1983 | Lim ........................ 435/1.1 |
| 5,286,495 | 2/1994 | Batich et al. .................. 424/490 |

OTHER PUBLICATIONS

Chang et al., 1995, Art Cells, Blood Subs, and Immob Biotech, 23:1–21.
Bourget et al., 1984, Applied Biochemistry and Biotechnology, 10:57–9.
Prakash et al., 1995 Biotechnology and Bioengineering, 46:621–6.
Prakash et al., 1993, Biomat, Art Cells & Immob Biotech, 21:629–36.
Enosawa et al., 1995, Dialog Information Services, File 73, EMBASE, Dialog Accession, No: 9615461; Japanese J Artificial Organs(Japan), 24/3(736–9).
Gardner et al (Applied Biochemistry and Biotechnology 10: 27–40, abstract only, 1984.*
Voet and Voet, In Biochemistry, Second edition, Wiley and Sons, Publishers. See pp. 670, 701, 720–722, 740, 756, especially Table 23–2 on p. 720), 1995.*
Wrong, Nature Medicine 3(1):3, 1997; see especially paragraph bridging cols. 2 and 3, Jan. 1997.*
Prakash and Chang (1993). Biomat. Art. Cells & Immob. Biotech 21(5): 629–636. See abstract, and paragraph bridging pp. 630 and 631.*
Prakash and Chang. Nature Medicine 2(8): 883–887, Aug. 1996.*

* cited by examiner

Primary Examiner—Karen M. Hauda
Assistant Examiner—Richard Schnizer
(74) Attorney, Agent, or Firm—Klauber & Jackson

(57) ABSTRACT

The present invention relates to a composition for oral administration to a patient for removal of undesired chemicals or amino acids caused by disease. The composition comprises an entrapped or encapsulated microorganism capable of removing the undesired chemicals or amino acids. The composition may comprise a pharmaceutically acceptable carrier for oral administration to the patient.

9 Claims, 10 Drawing Sheets

FIG_2

MICROENCAPSULATED GENETICALLY ENGINEERED MICROORGANISMS FOR CLINICAL APPLICATION

BACKGROUND OF THE INVENTION (a) Field of the Invention

The invention relates to a novel concept of using microencapsulated genetically engineered microorganisms for clinical application by oral administration.

(b) Description of Prior Art

Recent advancements in molecular biology have furnished a variety of genetically engineered microorganisms with many specialized functions. Unfortunately, it is difficult to use genetically engineered microorganisms for the treatment of patients.

Since parental administration of microorganism into human is too risky and dangerous, even if a very small amount is given.

In accordance with the present invention, this problem was solved by microencapsulating genetically engineered microorganisms and giving them orally. Microencapsulation prevents leakage of microorganism also if a small amount leaks out it is still safe since the gastrointestinal tract can safely contain non-pathogenic microorganism. The present invention describes a model study which can be used for a variety of genetically engineered microorganisms.

More particularly, the present invention demonstrates, as an example, the use of microencapsulated genetically engineered bacteria for the removal of urea and ammonia. Urea and ammonia removal is necessary in cases of kidney failure and liver failure, respectively. Uremia is caused by insufficient kidney function. As kidneys fails, substances normally excreted in the urine are retained in the blood and body tissues. This results in increased concentration of metabolites normally measurable in blood. For example, the blood urea nitrogen (BUN) level increases from 15 mg % to 100–300 mg %, and serum creatinine increases from 1.0 mg % to 10–25 mg %. Similarly, elevated level of ammonia in liver failure is evident. These substances in high concentrations become toxins or poisons and result in severe disturbances of metabolic pathways causing many diseases ranging from organ failure to impaired brain functions. Several attempts, including use of oral feeding of oxystarch and urease zirconium phosphate have been applied to remove these unwanted metabolites from the body fluid compartments without success. The amounts of oxystarch and urease-zirconium-phosphate needed were too large to allow for use in the routine treatment of the patients.

The microencapsulation concept is established to provide specialized environment to the living and non living encapsulated materials (Chang, T. M. S. (1964) *Science*, 146:524–525). In previous studies, it was shown that microencapsulated genetically engineered bacteria *E. coli* DH5 has great capacity to remove urea and ammonia from the artificial media and from the plasma in vitro (Prakash, S. and Chang, T. M. S. (1995) *Biotechnology and Bioengineering*, 46:621–626).

Surprisingly, and in accordance with the present invention, it is demonstrated for the first time that these microencapsulated genetically engineered microorganisms when given orally in very small amounts can effectively remove systemic urea and ammonia in kidney failure rats (Prakash, S. and Chang, T. M. S. (1996) *Nature Medicine*, 2(8):883–887). This capacity is much higher than any system available to date.

SUMMARY OF THE INVENTION

One aim of the present invention is to explore the possibility of using microencapsulated genetically engineered microorganisms for the treatment of various diseases by their oral feeding.

Another aim of the present invention is specific, and was directed to explore the potential of encapsulated genetically engineered bacterial cells for the treatment of kidney failure, liver failure and other diseases, which will serve as example for the application of this invention in clinical practice.

Earlier in vitro studies have shown that alginate-polylysine-alginate (APA) encapsulated genetically engineered *E. coli* DH5 cells is very effective in removing urea, without producing ammonia, and ammonia both from reaction media and plasma. However, at that time there was no way to safely used this in patients by parental injection (Prakash, S. and Chang, T. M. S. (1995) *Biotechnology and Bioengineering*, 46:621–626). The details of the process parameters of preparation of microcapsules and the kinetics of the in vitro studies are described in the same article (Prakash, S. and Chang, T. M. S. (1995) *Biotechnology and Bioengineering*, 46:621–626).

In accordance with the present invention there is provided a composition for oral administration to a patient for the removal of undesired chemicals and/or amino acids caused by a disease, which comprises a microorganism entrapped or microencapsulated to be capable of removing the undesired chemicals and/or amino acids in association with a pharmaceutically acceptable carrier for oral administration to the patient.

In accordance with one embodiment of the present invention, the composition consists in the microorganism which is microencapsulated using any microcapsule material which can retain the microorganism and allows the undesirable molecules for removal to enter the microcapsules.

The microencapsulating material which may be used in accordance with the present invention include, without limitation, nylon, silicon rubber, nylon-polyethylenimine, polylactic acid, polyglycolic acid, chitosan-alginate, cellulosesulphate-poly(dimethyldiallyl)-ammonium chloride, hydroxy-ethyl methacrylate-methyl methacrylate, chitosan-carboxymethyl-cellulose and alginate-polylysine-alginate.

In accordance with another embodiment of the present invention, the composition consists in the microorganism which is entrapped within a carrier using any entrapment material which can retain the microorganism and allows the undesirable molecules for removal to enter in contact with the entrapped microorganism.

The microorganism may be genetically engineered, such as, *E. coli* DH5 cells, among others.

The undesired chemical may be urea and/or ammonia, phenylalanine or tyrosine.

The diseases to be treated may be a kidney failure-causing disease, a liver failure-causing disease, hyperammonemia with elevated ammonia level, phenylketoneuria or tyrosinemia and melanoma among others.

DETAILED DESCRIPTION OF THE INVENTION

Safety concerns of introducing genetically engineered cells into the body have prevented their use in medical treatments. To solve this problem, polymeric membrane artificial cells containing genetically engineered cells were prepared in accordance with the present invention. When given orally, the cells remain at all time in the microcapsules and are finally excreted in the stool. During their passage through the intestine, small molecules such as urea diffuse rapidly into the microcapsules and are acted on by the genetically engineered cells. This lowers the high plasma urea level in kidney failure rats to the normal level. This also has exciting implications in the use of the present invention, including other types of genetically engineered cells for a number of medical applications.

In accordance with the present invention, there is taught the use of microencapsulated genetically engineered microorganisms for specific clinical applications and this through the oral administration of the microencapsulation.

More specifically, the efficiency of the microencapsulated genetically engineered microorganisms of the present invention for the removal of urea and ammonia from the body was tested using a model system of kidney failure. It was shown that this novel approach has the ability to lower systemic urea and ammonia better than any existing system. It is several hundred fold more efficient than the only presently available oxystarch or urease-zirconium-phosphate.

In addition to this example, other microencapsulated genetically engineered microorganisms can be used for oral administration to specifically remove specific unwanted amino acids such as, for example, phenylalanine in phenylketoneuria.

Suitable microorganisms which could be used in accordance with the present invention include, without limitation, Klebsiella aerogens for urea removal (UR), Proteous mirabilis for UR3, E. coli having gene for phenylalanine ammonia lyase (PAL) enzyme for phenylalanine removal (PR), E. coli having gene for PAL enzyme from Rhodosporidium toruboides for PR5, Providencia stuartil for UR6, and Bacillus pastteuri for UR.

In accordance with one embodiment of the present invention, alginate-polylysine-alginate microcapsules were used. However, many other types of microcapsules or entrapment methods for the microorganisms can also be used. For example and without limitation, microcapsules prepared from: nylon, silicon rubber, nylon-polyethylenimine, polylactic acid, polyglycolic acid, chitosan-alginate, cellulosesulphate-poly(dimethyldiallyl)-ammonium chloride, hydroxy-ethyl methacrylate-methyl methacrylate, chitosan-carboxymethyl-cellulose.

Figure 1:
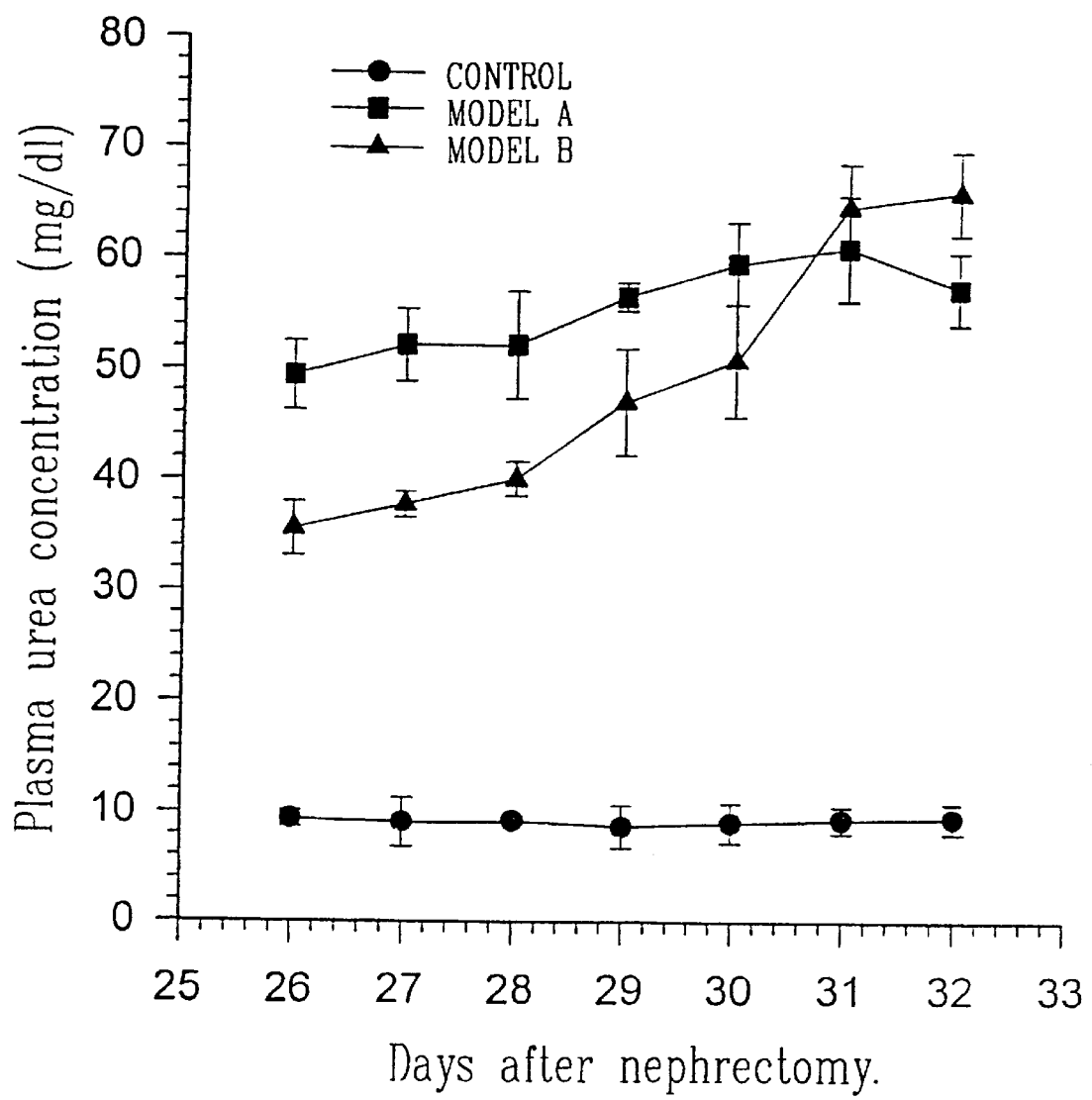
FIG. 1 is a graph of the urea profile of uremia rat models.

To evaluate any possible clinical application of the present invention a suitable animal model was required. Accordingly, one first goal was to obtained a suitable experimental rat model for uremia. Two different approaches were used to make a suitable animal model, which were identified as Models A and B. The rat used for making models were male Wister rats of 300–325 g weight range. The details of the procedure are described below. Result shows (FIG. 1) that model A stands better ($P=0.0001323$, degree of freedom=6, paired student t-test). Model A comprises a unilateral right nephrectomy and partial unilateral left artery, vein, ureter ligation.

Chemicals:

Alginic acid (low viscosity, Lot 611994) and poly-L-lysine (MW 16,100, Lot 11H5516) were purchased from Kelco and Sigma Chemical Co. (St. Louis, Mo., USA) respectively. Unless specified, chemicals were obtained commercially and not further purified before use and they were of analytical reagent grade.

Microorganism and Culture Conditions:

Genetically engineered bacteria Escherichia coli DH5, containing the urease gene from Klebsiella aerogens, was used. Luria-Bertani (LB) growth medium was used for primary cell cultivation. The composition of LB medium was of 10.00 g/L bactotryptone (Difco), 5.00 g/L bacto yeast extract (Difco), and 10.00 g/L sodium chloride (Sigma). The pH was adjusted to 7.5 by adding about 1.00 ml of 1.00 N NaOH. Media were then sterilized in Castle Labclaves for 30 minutes at 250° F. Incubation was carried out in 5.00 ml LB in 16.00 ml culture tubes at 37° C. in an orbital shaker at 120 rpm. For the large-scale production of biomass, for microencapsulation purpose, 250 ml Erlenmeyer flask containing 100 ml LB medium was used.

Microencapsulation Procedure:

Very briefly, alginate-poly-L-lysine-alginate (APA)-microcapsules containing E. coli DH5 cells were prepared as follows.

Figure 11A:
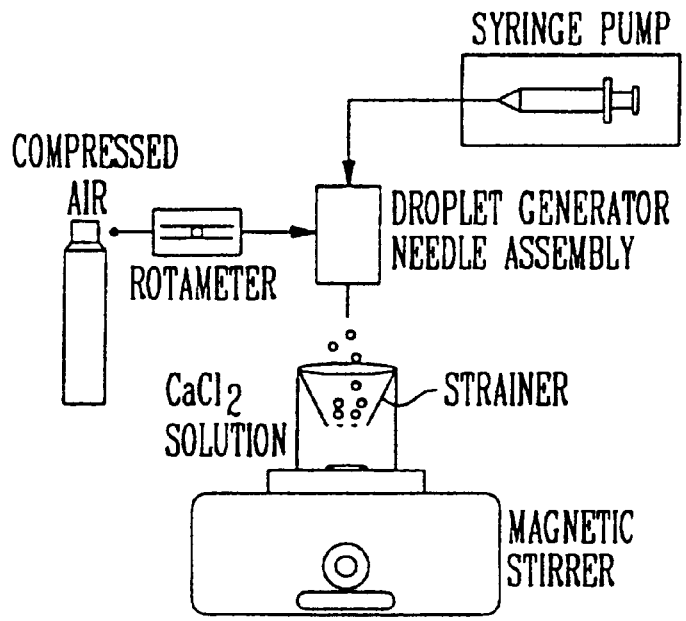
FIGS. 11A and 11B illustrate a schematic representation of the microencapsulation apparatus set-up.
Figure 11B:
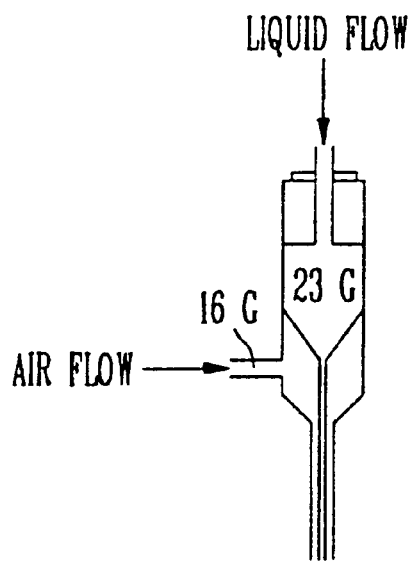

Bacterial cells were suspended in an autoclaved sodium alginate in 0.9% sodium chloride solution. The viscous alginate-bacterial suspension was pressed through a 23-gauge needle using a syringe pump (Compact Infusion Pump Model 975™, Harvard App. Co. Mass.). Compressed air through a 16 gauge needle was used to shear the droplets coming out of the tip of the 23-gauge needle. The two needles in combination make up the droplet needle assembly in FIGS. 11A and 11B. The droplets were allowed to gel for 15 minutes in a gently stirred ice-cold solution of calcium chloride (1.4%). After gelation in the calcium chloride, alginate gel beads were coated with polylysine (0.05% in HEPES™ buffer saline, pH 7.20) for 10 minutes. The beads were then washed with HEPES™ and coated with an alginate solution (0.1%) for 4.00 minutes. The alginate-poly-L-lysine-alginate capsules were then washed in a 3.00% citrate bath (3.00% in 1:1 HEPES™-buffer saline, pH 7.20) to liquefy the gel in the microcapsules. The microcapsules formed were stored at 4° C. and used for the experiments.

Microcapsule Storage Condition:

After the microencapsulation microcapsules were washed properly several times (two to three times) with sterile water.

The microcapsules were resuspended in the Agrobacterium minimum broth (AG minimal media) at 4–10° C. This media, unlike LB media, does not support the growth of E. coli, it has however all the components which is necessary to maintain biochemical activity. Before the use microcapsules were washed in normal saline and used for the experiment.

Reaction Media for in vitro Urea and Ammonia Removal Experiments:

Reaction media in all experiments consisted of 1.00 g/L glucose, 20.00 mg/L magnesium sulfate, 30.00 mg/L dipotassium monohydrogen phosphate, and 0.07 mg/L vitamin $B_{12}$. As required, filtered sterilized urea was added in the reaction media to make the urea concentration 100 mg/dl. Plasma from a bovine source was used for the plasma urea and ammonia removal experiments and filter-sterilized urea was added to the plasma. This was done to mimic the uremic patient's plasma characteristics in vitro.

Surgical Model of Uremia (Rat)

Two different surgical models were developed and identified as model A and model B. In both the models male Wister rats with weight range 300–340 g were used. The details of the surgical procedure applied to prepare uremia rat models are as follows.

Model A:

A two-step procedure, one to perform right nephrectomy and other to partially ligate the left artery, vein and ureter, is required. The details of the procedure are as follows.

i) Unilateral (Right) Nephrectomy:

The anesthetized animal is placed in ventral recumbency with its tail towards the surgeon. The hair in the right dorsal lumber area is clipped and the skin swabbed thoroughly with surgical scrub: A 2–3 cm incision is made into the skin caudal to the rib cage on the right side of the animal. A 2–3 cm incision is then made into the underlying muscle wall. The kidney is pooled through the muscle wall, the renal artery, vein and ureter are ligated and the kidney is removed by incising the vessels and ureter between the kidney and the ligature remaining tissue is returned to the peritoneal cavity and the muscle wall is sutured. The skin incision is closed with 2–3 wound clips.

ii) Unilateral (Left) Renal Artery/Vein/Ureter/Ligation:

The left side of the rat is prepared as if to perform a left nephrectomy. After an incision (2–3 cm) is made in the muscle wall, the left renal artery, vein, and ureter are located. Using blunt forceps, the left renal vessels and ureter are isolated and separated from the peritoneal connective tissue. The renal vessels and ureter are partially ligated using sterile silk suture. The muscle wall is sutured. The skin incision is closed with 2–3 metal wound clips.

Model B:

Left Renal Artery/Vein/Ureter/Ligation:

The anesthetized animal is placed in ventral recumbency with its tail towards the surgeon. The hair in the left dorsal lumber area is clipped and the skin swabbed thoroughly with surgical scrub. A 2–3 cm incision is made into the skin caudal to the rib cage on the left side of the animal. A 2–3 cm is then made into the underlying muscle wall and the left artery, vein, and ureter are located. Using blunt forceps, the left renal vessels and the ureter are isolated and separated from the peritoneal connective tissue. The left renal vessels and ureter are ligated using the sterile silk suture. The muscle wall is sutured. The skin incision is closed with 2–3 metal wound clips.

Discussion:

The main objective of present invention is to explore the potentials of a novel approach to treat various diseases using microencapsulated genetically engineered microorganisms given orally. The specific objective of this research is to find a suitable means to manage urea and ammonia level in kidney failure and liver failure. Accordingly, in accordance with the present invention, encapsulated genetically engineered E. coli DH5 cells that contain urea utilizing urease gene from Klebsiella aerogens within an APA membrane were prepared and premise to use them by oral administration.

In accordance with the present invention, it is shown that microencapsulated genetically engineered microorganisms can be used orally to treat kidney failure rats to lower their body urea and ammonia levels. Further, we are also first to report that oral feeding of both APA-encapsulated and free bacteria reduces the plasma urea in experimental uremic rat models. When these were evaluated, using the single pool model, it was found that encapsulated bacteria can remove urea with much greater efficiency than generally used oxystarch and urease-zirconium phosphate. A quantity of 3.2±0.67 mg of urea/mg of biomass on the day second and 8.00±1.39 mg/mg of biomass on the day four was observed for the encapsulated bacteria. Oxystarch and urease-zirconium-phosphate on the other hand has a capacity to remove 0.103 mg of urea/mg oxystarch and 0.033 mg of urea/mg of urease-zirconium-phosphate only (Prakash and Chang (1995) *Biotechnology and Bioengieering*, 46:621–626). Also the current oxystarch and urease-z.p. system works under specialized conditions which is not necessarily available during the actual treatment. For example oxystarch has good capacity of urea and ammonia binding at a specific pH only.

Quick removal of ammonia from the body fluid compartment is required to prevent neurological damages during liver failure. In accordance with the present invention, it was shown that ammonia removal is possible by encapsulated bacteria. Plasma ammonia concentration of uremic rat fell from 519–560±51$\mu$M/L to 144±24.70$\mu$M/L during the urea removal experiment. This is a decrease of about 73.30±4.57%.

Figure 8:
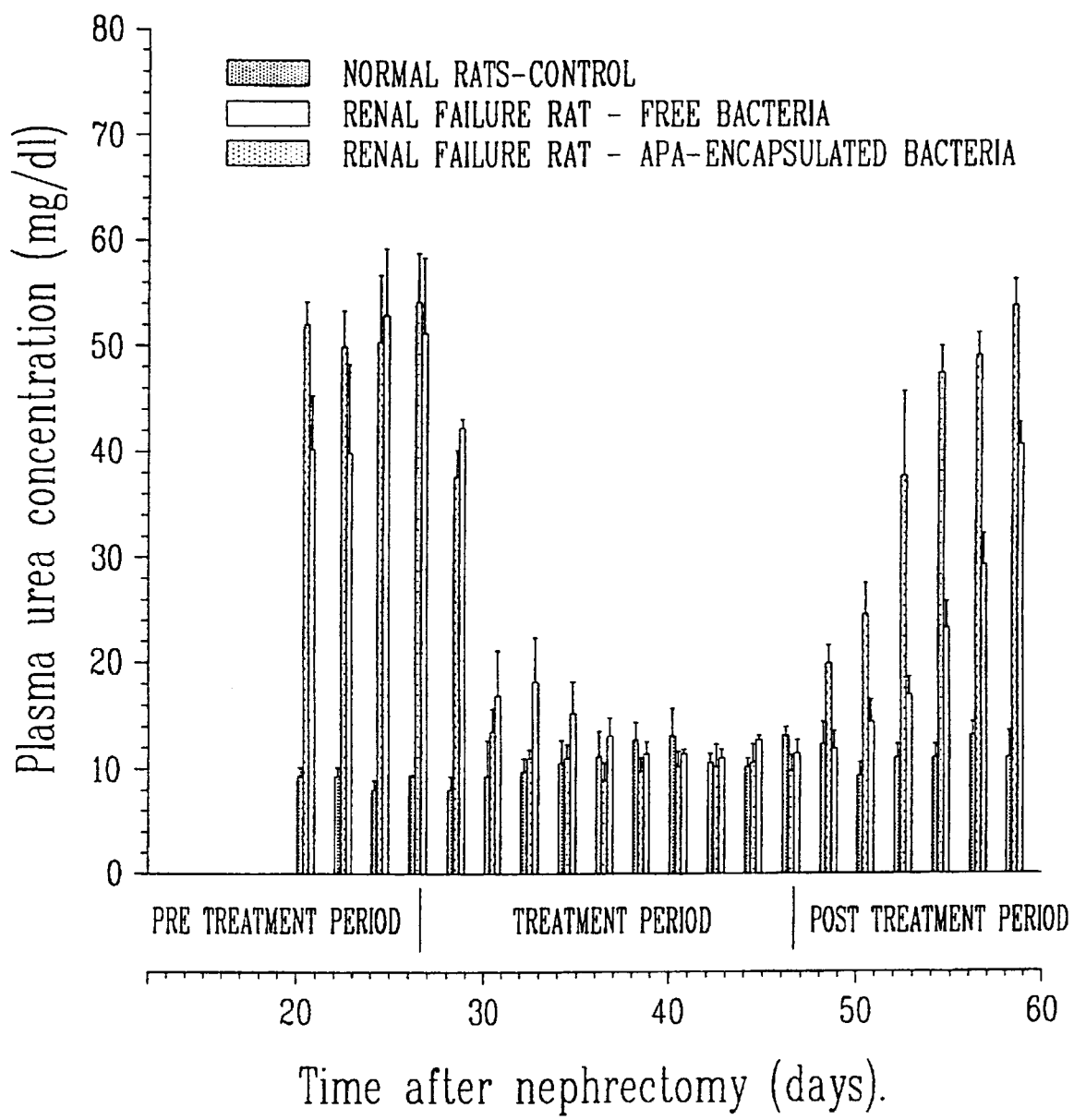
FIG. 8 is a graph of the comparative study of urea removal by oral feeding of free and APA-encapsulated bacteria.

The behavior of the APA-encapsulated bacteria of the present invention and free cells in terms of urea removal (FIG. 8) indicates clear advantages of using encapsulated bacteria over free bacteria. At the onset of the treatment period free bacteria has less urea depletion capacity than microencapsulated bacteria. This is because of the death of the free bacteria during the intestinal passage. In any treatment which requires using microorganisms, it is important to be sure that the microorganisms do not stay in the body. Thus microencapsulated microorganisms are excreted in the feces. Thus as soon as feeding is discontinued urea produced by the body in the uremic rat resulted in the increase of urea level to the pretreated uremic level. On the other hand when the treatment was stopped for free bacteria they continue to stay in the body and continue to keep a low urea level for some time (FIG. 8). Again the encapsulated microorganism shows the advantage of being removed quickly over the free microorganism.

This study demonstrates the therapeutic efficacy of oral feeding of microencapsulated genetically engineered microorganisms in general and genetically engineered bacteria in particular. This study also provides the foundation of the development of oral microcapsules containing genetically engineered bacteria as an easily administrable oral form for the treatment of kidney failure, liver failure and other diseases.

The present invention will be more readily understood by referring to the following example which is given to illustrate the invention rather than to limit its scope.

EXAMPLE I

Urea and Ammonia Removal by Oral Feeding of Microencapsulated Genetically Engineered Bacteria Experimental Procedure:

The bacteria were grown in LB medium. Log phase bacterial cells were harvested by centrifuging at 10,000 g for 20 min. at 4° C. The cell mass was then washed five times with sterile cold water to remove media components. Cells were then weighed and used for the urea and ammonia removal studies by free bacteria. For the microencapsulated urea and ammonia removal studies the equivalent masses of the cells were microencapsulated and used. In all the experiments, the ratio of the reactor volume to the amount of microencapsulated bacteria used was held constant.

For the microencapsulated in vivo animal studies, microcapsule containing log phase genetically bacteria were first suspended in 0.8–1.0 ml sterile normal saline in a 5 ml syringe. The floating microcapsules were then forced fed orally to the uremic rats using a curved 12G–3½ stainless steel needles. A quantity of 11.15±2.25 mg/kg body weight of log phase genetically engineered bacteria $E.\ coli$ DH5 cells in Microcapsules was used. The sampling were done by taking blood sample out from the rat tail after sedating them using appropriate amount of drugs that has been reported of not having any side effects on renal or hepatic functions. The drug used were ATRAVET™ (acepromazine) and KETASET™ (ketamine) with the concentration of 75 mg/kg and 5–10 mg/9 kg intramuscularly, respectively. A small 23 G1 precision GLIDE™ needle and 10 CC syringe. Blood sample were centrifuged immediately using an EPPENDORFF™ and plasma were collected and analyzed for urea and ammonia.

Figure 2:
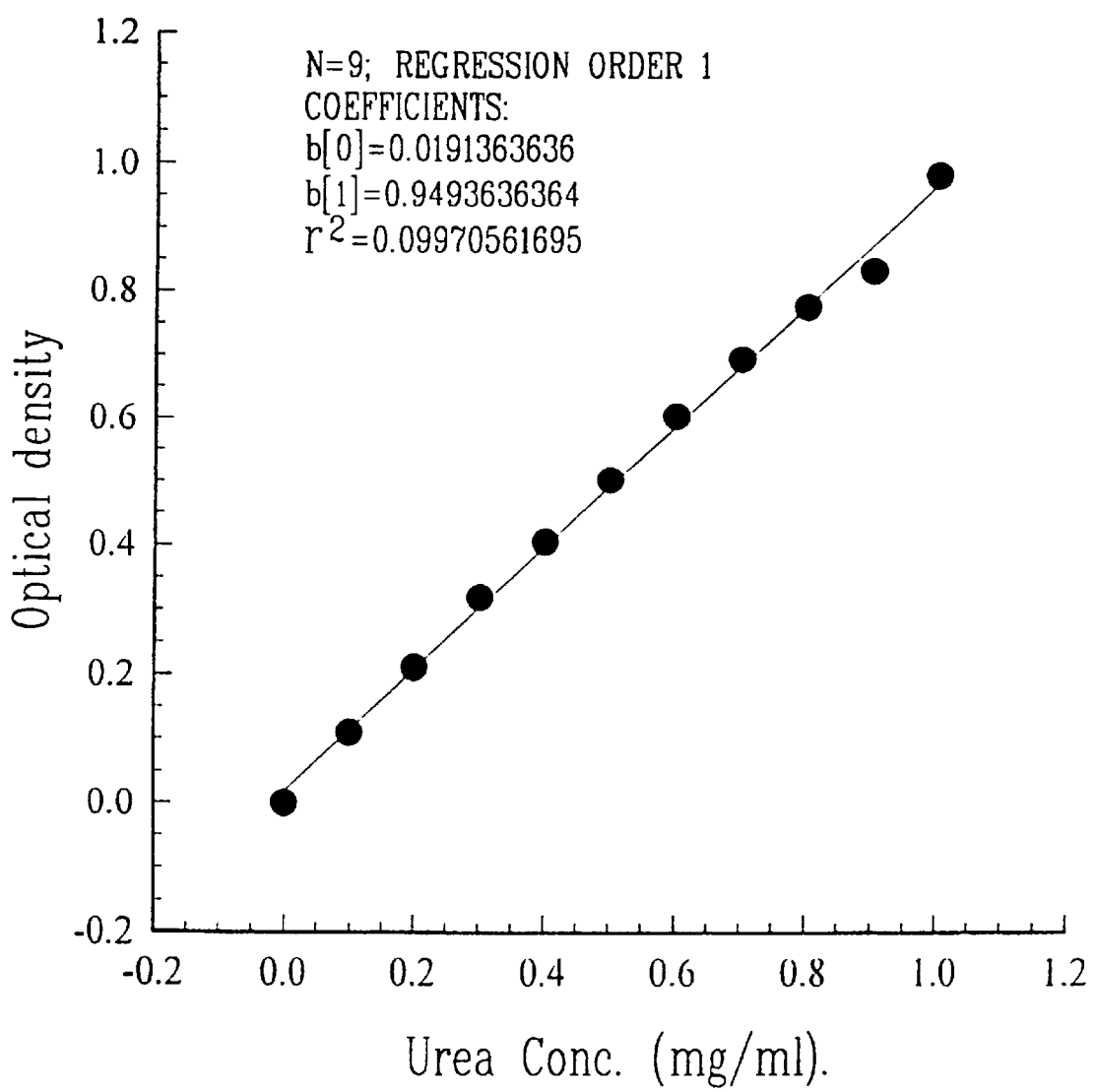
FIG. 2 illustrates a standard curve for plasma urea determination.

Urea Determination:

Urea concentrations were determined based on quantitative measurements of blood using the BUN kits purchased from Sigma Chemical Co. USA and PERKIN ELMER LAMBDA™ 4B UV/Spectrophotometer. The method used allows for the determination of serum or plasma urea without deproteinization. In the method, a reaction of urea with diacetyle monooxamine gives a pink color chromogen and hydroxylamine. The urea concentration is directly proportional to the intensity of the color produced, which can be measured spectrophotometrically between 515–540 nm. This method is simple, rapid, highly sensitive, and is not influenced by the presence of ammonium ions. A standard curve, for the determination of urea, using the known quantity of the standard urea solution and optical density at 540 nm was prepared (FIG. 2). This standard curve was used in all the experiments to quantify the urea.

Ammonia Determination:

Ammonia was analyzed using a fluorescent light scattering MULTISTAT™ III microcentrifugal analyzer. The system used was Instrumentation Laboratories, MULTISTAT™ III plus (Spokane, Wash.), microcentrifuge analyzer (MCA) in the absorbance mode (Sigma procedure, catalogue 170-UV). This measurement was based on the reductive amination of 2-oxoglutarate, using glutarate dehydrogenase (GLDH), and reduced nicotinamide adenine dinucleotide (NADH). The decrease in absorbance at 340 nm due to the oxidation of NADH is proportional to ammonia concentration. This method requires preparation of a fresh standard curve each time and accordingly a standard curve was prepared each time.

Results:

This study was design to explore the use of microencapsulated genetically engineered microorganisms for the treatment of various diseases by oral feeding. This study more specifically assesses the future potential of encapsulated genetically engineered bacterial cells for the treatment of kidney failure, liver failure and other diseases in clinical practice.

Earlier in vitro studies demonstrated that alginate-poly-L-lysine-alginate (APA) encapsulated genetically engineered $E.\ coli$ DH5 cells are very effective in removing urea and ammonia both from reaction media and plasma (Prakash, S. and Chang, T. M. S. (1995) $Biotechnology\ and\ Bioengineering$, 46:621–626). The details of the involved process parameters in preparing microcapsules and in vitro kinetics of urea and ammonia removals are described in that paper.

Figure 3:
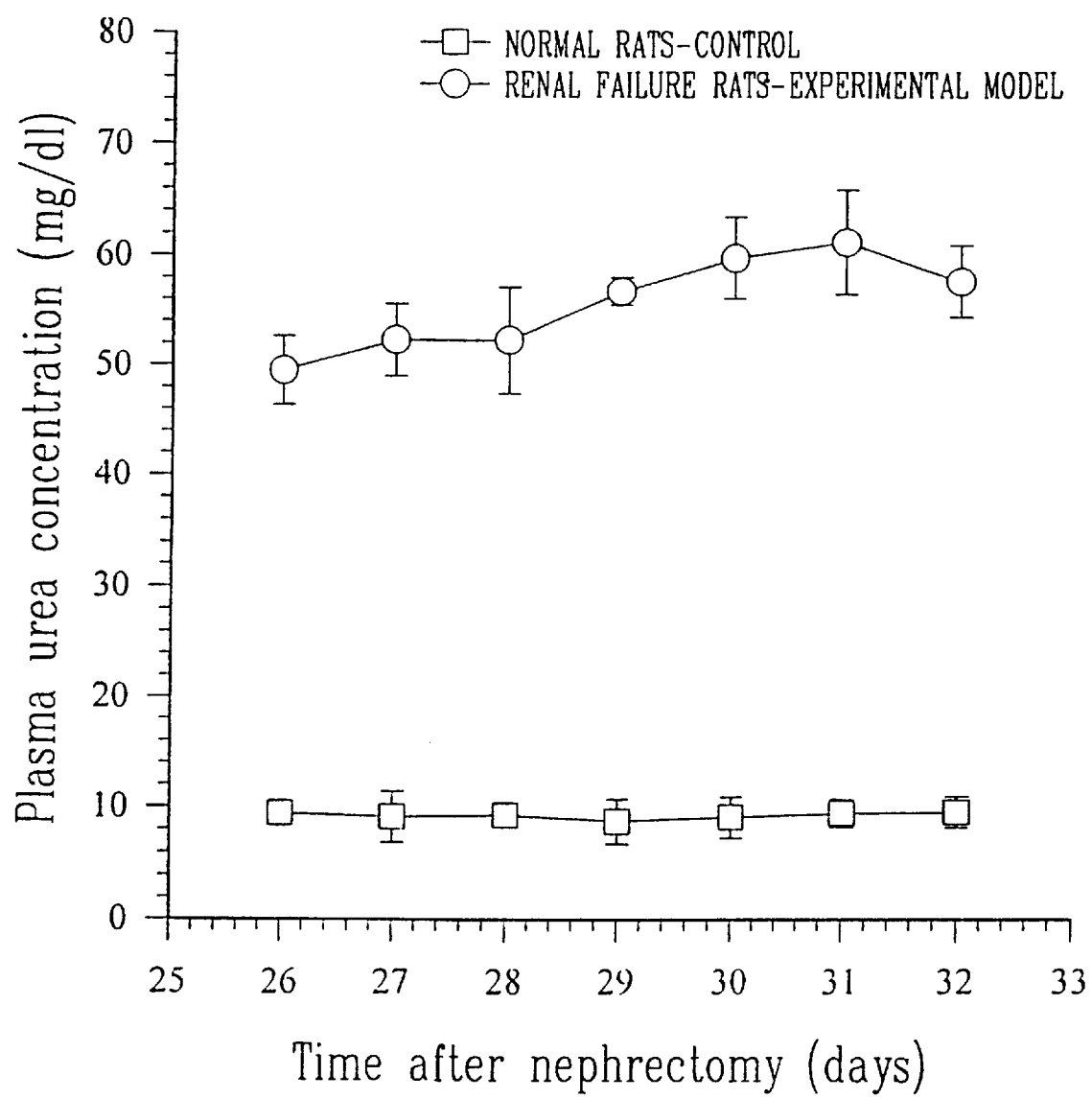
FIG. 3 is a graph of plasma urea as a function of time in normal control rats and experimental uremic rat models.
Figure 4:
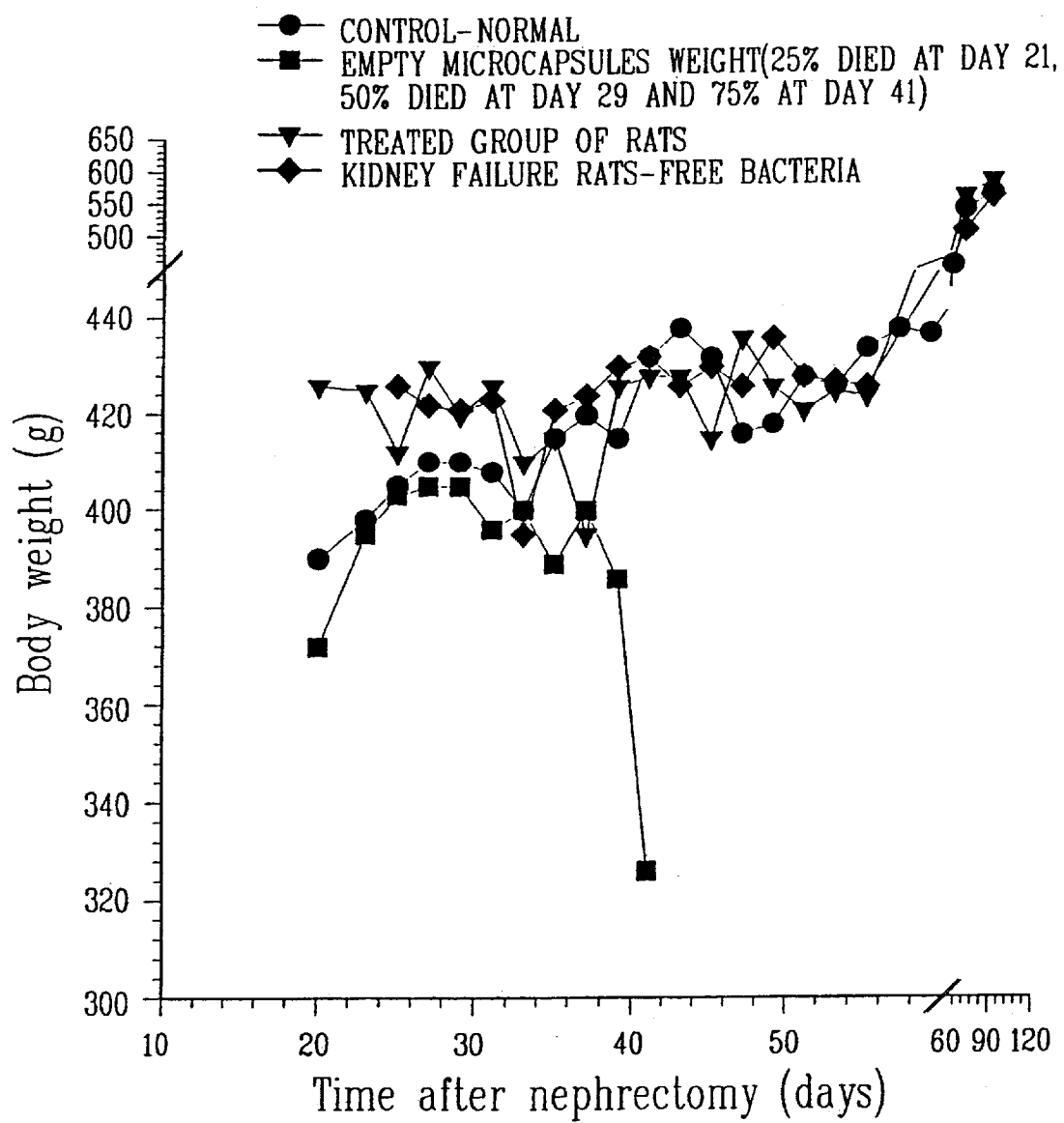
FIG. 4 is a graph of weight profile of normal control rats and experimental uremic rat models.

To evaluate any possible clinical application of this invention a suitable animal model is required. Consequently, a first goal was to obtain a suitable experimental rat model for uremia. A surgical method to make a suitable uremic rat model was designed. The rat used for making models were male Wistar rats of 300–325 g weight range. Results shows that the procedure is a successful method to make uremic rat model. Partial ligation resulted in different degrees of destruction of kidney tissues. As a result in these experimental rat models a large variation in the plasma urea concentration was observed, ranging from a plasma urea of as low as 17.61±1.2 mg/dl and as high as 172.28±40 mg/dl. For the experiments, only animals with plasma urea of 52.08±2.06 mg/dl were used. This uremic rat model has a high level of plasma was compared to normal rats (FIG. 3). Furthermore, they can survive for enough time for our experiment. This model is based on right nephrectomy followed by partial left artery, vein, ureter partial ligation. The weight profile of the experimental rats was followed and results are shown in FIG. 4. The main objective for the present study was to have an animal renal failure model that can survive long enough for the experiment to see whether oral administration of encapsulated genetically engineered $E.\ coli$ DH5 can decrease the systemic urea level.

Figure 5:
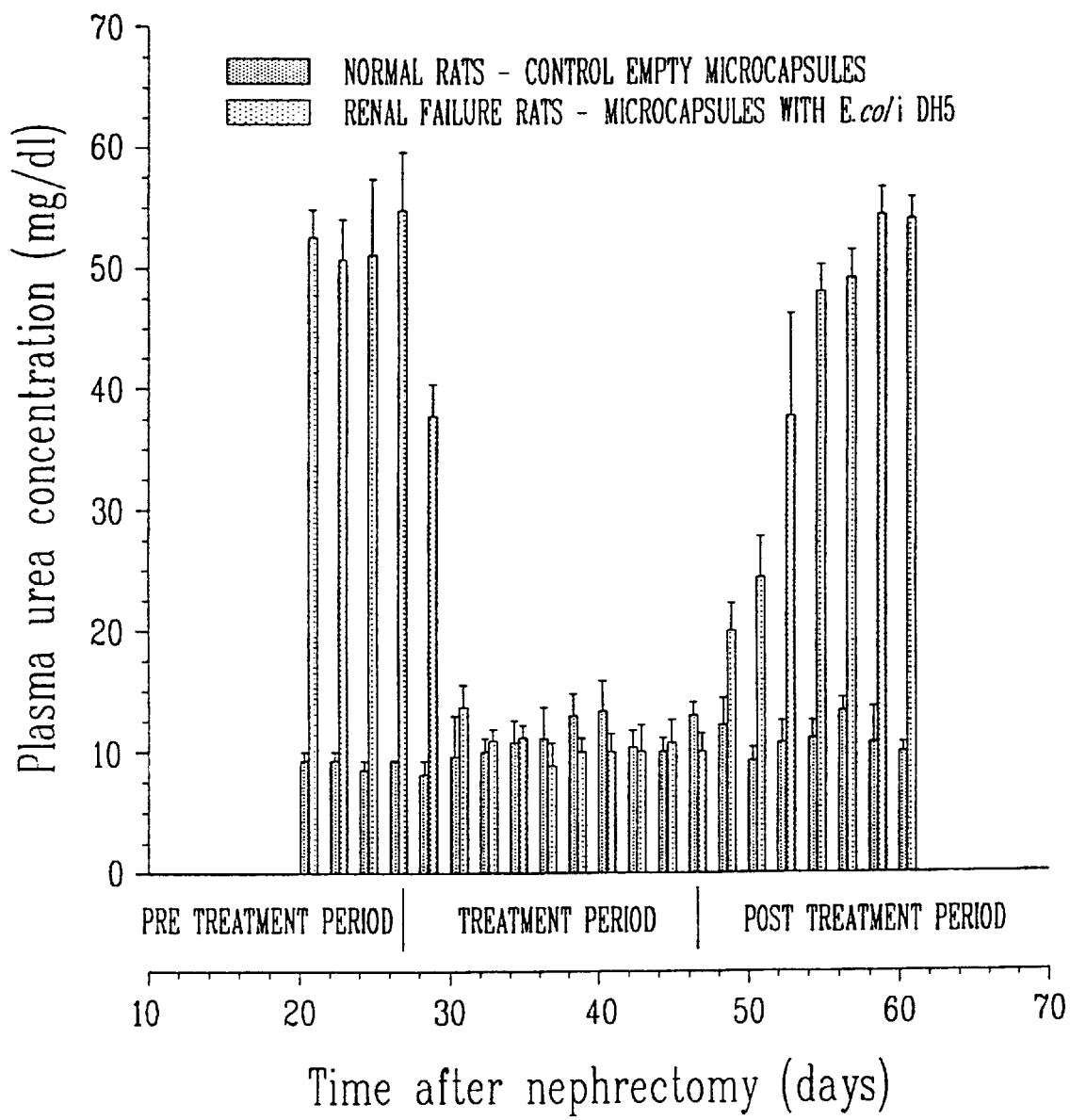
FIG. 5 is a graph of the urea removal profile of APA-encapsulated bacteria in experimental uremic rat models.

Experiments were designed to evaluate the use of microencapsulated genetically engineered cells for the removal of urea in uremic rats. The experimental model described earlier was used for this study. Beside monitoring pretreatment urea level in experimental rats as self control, normal rats and uremic rats receiving empty microcapsules containing no bacteria were both used as control. During all the experimental studies both control and nephrectomy rats were fed with regular chow containing 22.5% protein (Purina Mills, LaSalle, Qc). A quantity of 11.15±2.25 mg/kg body weight of log phase alginate-poly-L-alginate microencapsulated bacteria were forced fed daily to a group of 26 days old nephrectomy rats with an elevated level of plasma urea; a plasma urea concentration of 52.08±2.06% mg compared to normal rat plasma urea level which is 9.10±0.71% mg. Results in FIG. 5 show that bacteria were able to lower plasma urea concentration from 52.08±2.06 to 37.53±3.31 mg/dl in the first 48 hours of treatment, to 13.34±2.24 mg/dl the day after and to 10.58±0.85 mg/dl on day 7. When daily feeding treatment was continued, we were able to maintain plasma urea level in uremic rats very close to normal values for a period of as long as 21 days. A return to high urea level is observed when the treatment was stopped. Urea level went back to the 20.11±1.80 mg/dl, on very next day followed by 24.52±3.25 mg/dl, 37.60±8.21 mg/dl, 47.57±2.26 mg/dl, 48.92±2.09 mg/dl, 53.80±2.18 mg/dl, and 53.69±2.59 mg/dl on days 2,3,4,5,6, and the day 7, respectively. Two animals were died on day 8 of cessation of treatment. A dissection study showed a typical uremic death with symptoms of hemorrhagic gut, conjugated and collapsed lungs, and the chest cavity filled with fluid. Urea concentration in the lung fluid reached as high as 177.21±12.90 mg/dl (n=2). Further, 50% of the all the animals died within the first 29 days of the cessation of treatment.

Figure 6:
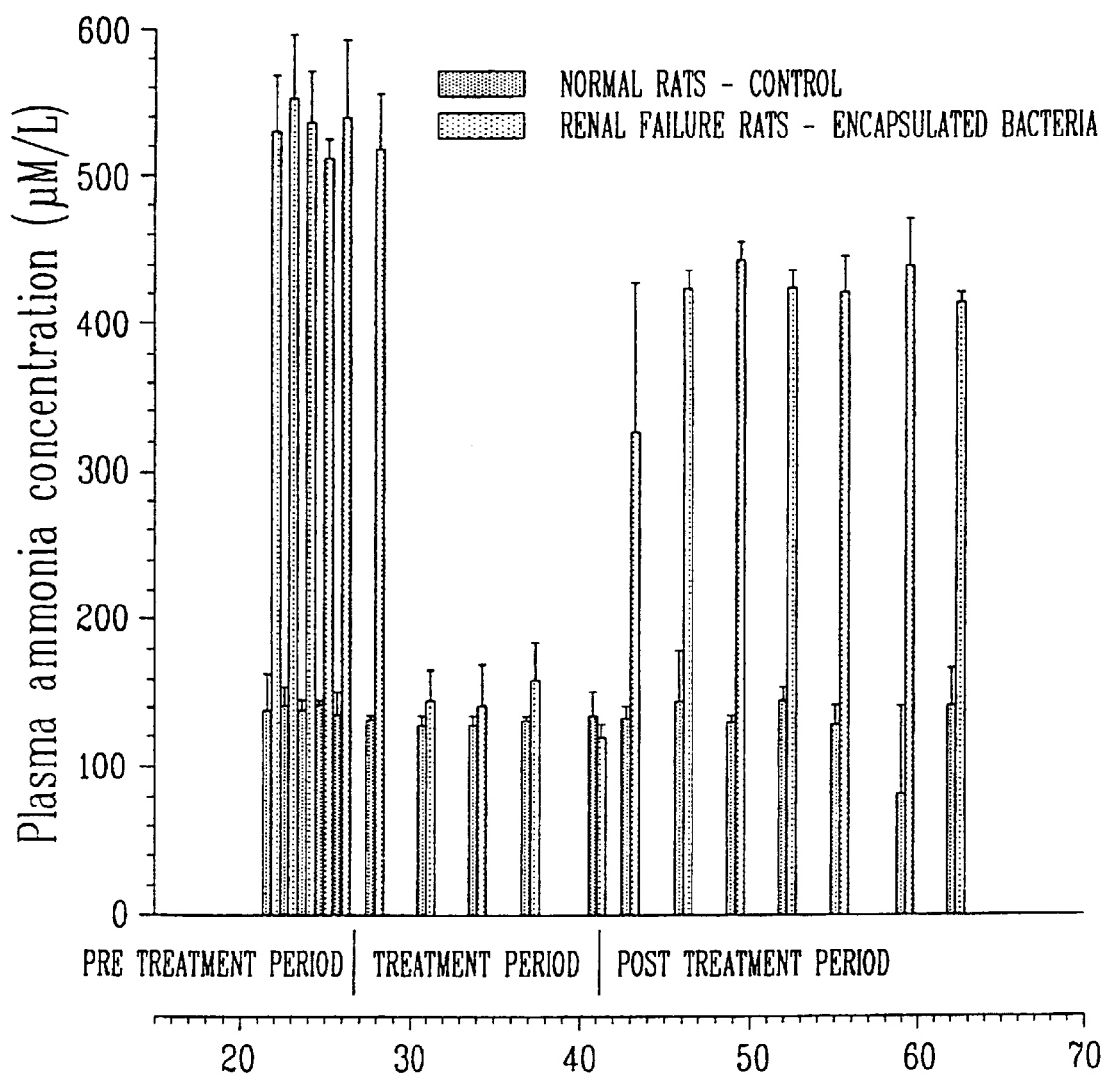
FIG. 6 is a graph of the ammonia profile of uremic rat before, during, and after treatment by oral feeding of APA-encapsulated genetically engineered bacteria for urea removal.

Analogous experiments were done to observe the fate of ammonia during urea removal by APA encapsulated genetically engineered *E. coli* DH5 cells. This was also done to evaluate the possible use of this system in liver failure. Results (FIG. 6) show that the ammonia level which was always present in the range of 539±51 mM decreases to 144±24.70 mM and remained constant in the entire period of treatment.

Figure 7:
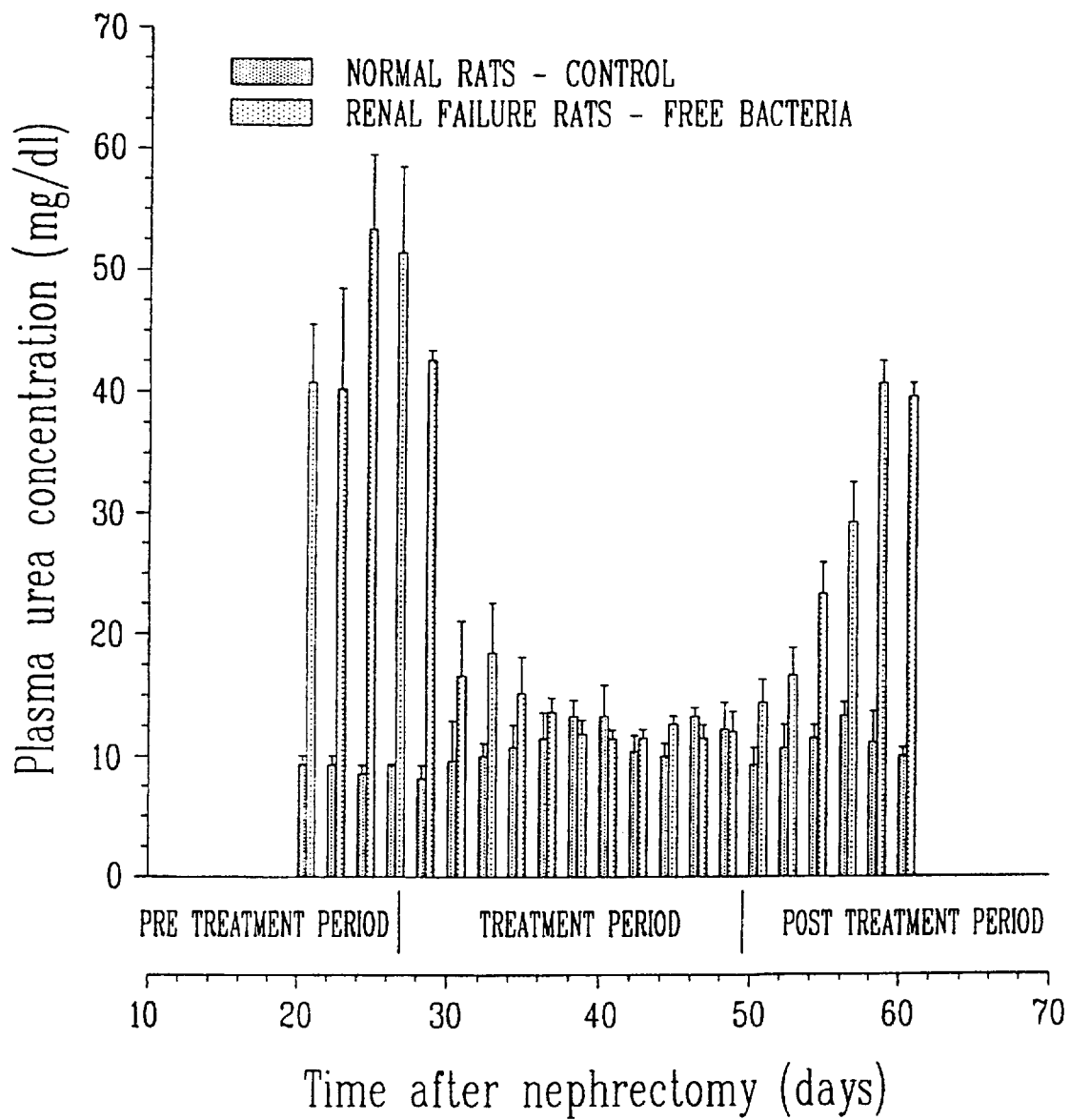
FIG. 7 is a graph of the urea removal profile of free bacteria in experimental uremic rat models.

The data obtained in FIG. 7 show that free bacteria were also able to deplete plasma urea. During the experiment with free cells, the amount of bacteria used was the same as in the APA microencapsulated studies. When we compare the urea removal kinetics of free bacteria with APA encapsulated bacteria (FIG. 8) we found that the overall kinetics to be similar. However, at the outset, the rate of urea removal by free bacteria was much smaller than that by APA encapsulated bacteria. Free bacteria removes 20.28±1.06% on the first day and 68.29±4.30% on the second compared to 36.34±4.70% and 80.49±2.96% by APA-encapsulated bacteria. Furthermore, during post treatment period the rate of increase of plasma urea concentration in APA encapsulated bacteria is much higher than that observed with free bacteria.

Figure 9:
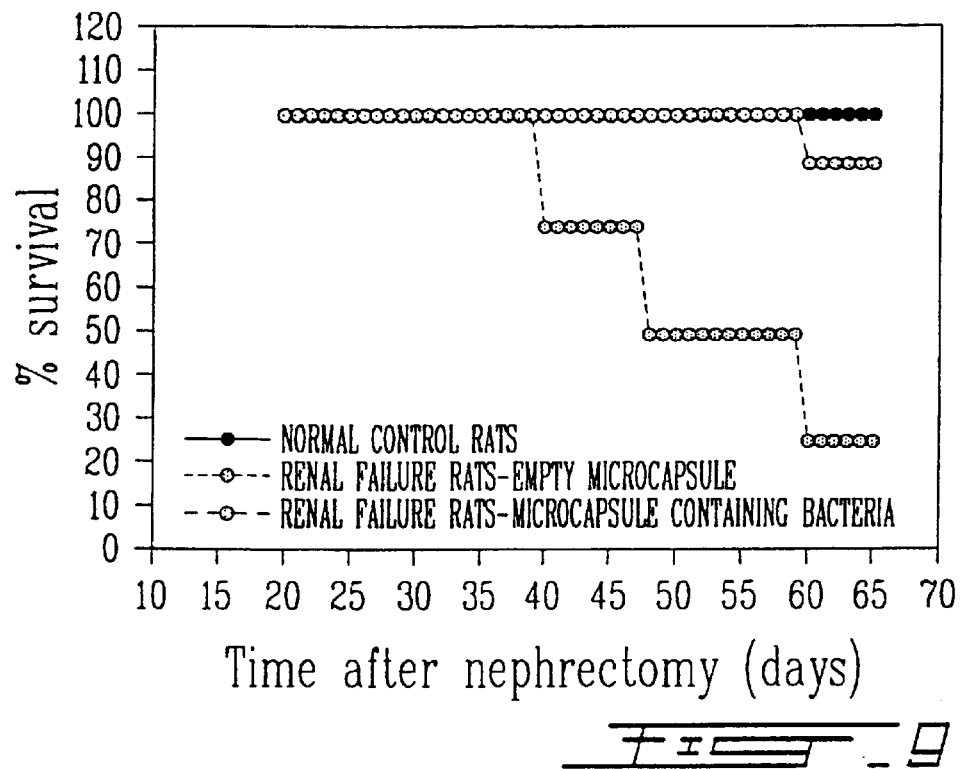
FIG. 9 illustrates survival curve for control rats and experimental renal failure rats receiving empty APA microcapsules and APA microcapsules with genetically engineered bacteria E. coli DH5 cells.

Experiments were also designed to follow the long term treatment effect. Results are plotted as survival curve for the treated experimental rat models (FIG. 9). Result shows that all the treated animal were survived compared to 50% survival for the untreated animals for the first 27 days of the treatment. Result also shows a very high survival rate in the treated group of the animals, up to 87.5% in the treated group of animals receiving orally administered microencapsulated genetically engineered bacteria compared to experimental renal failure rat groups which shows very low survival. The renal failure experimental rat groups which were not receiving only empty microcapsules 25% animal died in the first 21 days, 50% died after 29 days, and 75% animal died after 41 days.

Figure 10:
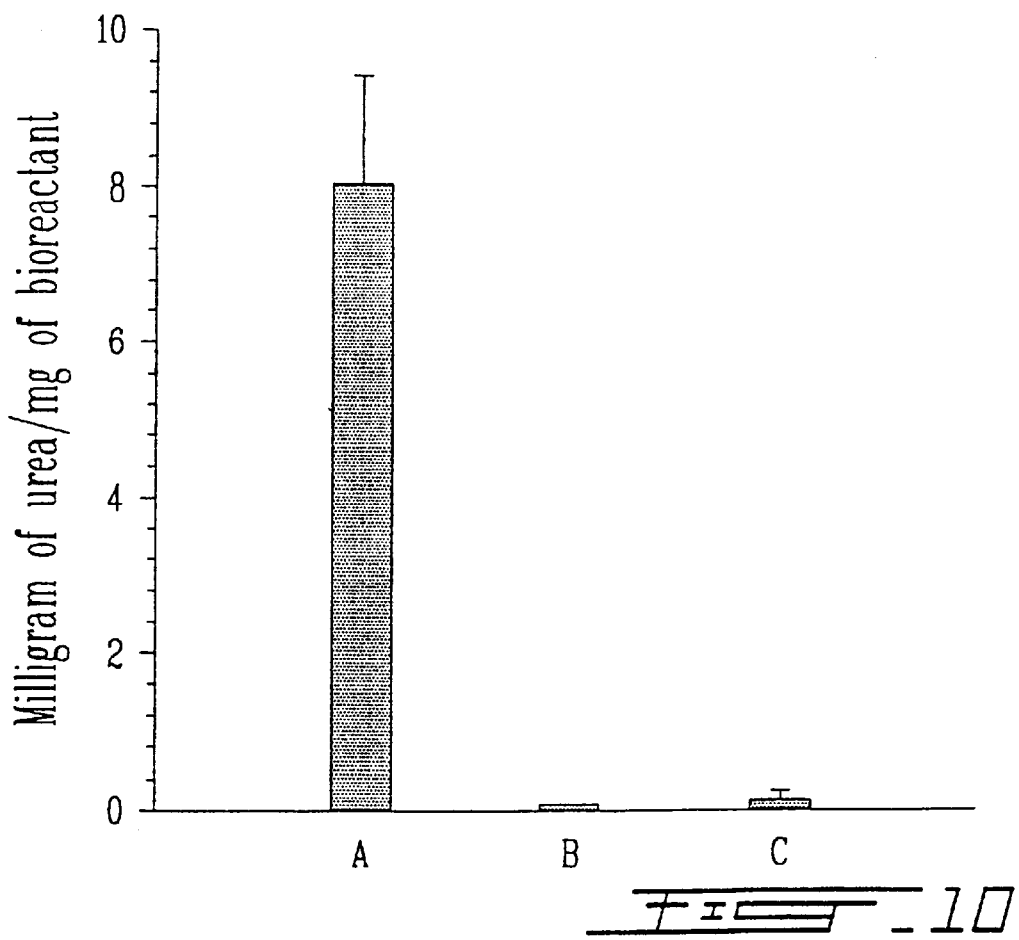
FIG. 10 is a graph of the comparative study of urea removal efficiency of APA-encapsulated bacteria, urease-zirconiumphosphate and oxystarch.

Using a single pool model, the urea removal by APA encapsulated genetically engineered bacteria was calculated and compared it with other available counterpart oral adsorbents in FIG. 10. Calculations show that oral administration of a biomass of 4.2 g/day to a 70 kg man would lower the plasma urea concentration from 100 mg/dl to 10 mg/dl. This is a very small amount administered compared to the amounts of about 388 g oxystarch and 1212 g of microencapsulated urease-zirconium phosphate required to lower the plasma concentration from 100 mg/dl to 10 mg/dl in patients. The required dosages for oxystarch and microencapsulated urease-zirconium phosphate are too large to allow them for routine daily use in patients. On the other hand, our study shows that a very small amount of microencapsulated genetically engineered *E. coli* DH5 cells can maintain a normal urea level in uremic rats.

Conclusion:

This Example describes a new method for the removal of urea and ammonia by oral feeding of microencapsulated, genetically engineered bacterial cells.

The APA-encapsulated genetically engineered *E. coli* DH5 cells efficiently lower the urea from the body fluid compartments of the uremic rat model. Urea depletion was better by the microencapsulation process as microencapsulation protects the microorganism in the gastrointestinal tract. Encapsulated bacteria was able to reduce 36.34±4.70% of the total plasma urea within first 48 hours and 80.49±2.96% of plasma urea on the day second. Under similar conditions, the same bacteria can also lower plasma ammonia from 519±51.26 μM/L to 144.00±24.70 μM/L in the 48 hours of the treatment. Bacterial cells do not produce ammonia and use urea for its metabolic nitrogen requirement. The present invention shows that this novel approach is several hundred folds more efficient for removing urea and ammonia than the standard oxystarch and urease-zirconium phosphate approaches. The present invention, therefore, shows the initial therapeutic feasibility of oral feeding of microencapsulated genetically engineered bacteria *E. coli* DH5 cells for the removal urea and ammonia uremia in experimental uremic rats. The present invention also provides the foundation for the development of oral microcapsules containing other types of genetically engineered cells for future clinical applications.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of reducing the concentration of ammonia or urea, or both ammonia and urea, in a mammal comprising orally administering genetically engineered bacteria *Escherichia coli* DH5 which comprise the urease gene from *Klebsiella aerogens*, wherein said bacteria are entrapped or microencapsulated in alginate-poly-L-lysine-alginate microcapsules, and are further contained in a pharmaceutically acceptable carrier, wherein the administration of said genetically engineered bacteria results in the removal of said ammonia or urea, or ammonia and urea, from said mammal.

2. The method of claim 1 wherein said microorganism is microencapsulated using any microcapsule material which can retain the microorganism and which allows urea and ammonia to enter the microcapsules.

3. The method of claim 1 wherein said microorganism is entrapped within a carrier using any entrapment material which can retain the microorganism and which allows urea and ammonia to enter the microcapsules.

4. The method of claim 1, wherein said ammonia or urea is caused by a disease.

5. The method of claim 4, wherein said disease is a kidney-failure-causing disease.

6. The method of claim 4, wherein said disease is a liver-failure-causing disease.

7. The method of claim 4, wherein said disease is hyperammonemia with an elevated ammonia level.

8. The method of claim 2 wherein said microorganism is microencapsulated using any material selected from the group consisting of nylon, silicon rubber, nylon-polyethylenimine, polylactic acid, polyglycolic acid, chitosan alginate, cellulosesulphate-poly(dimethyldiallyl) ammonium chloride, hydroxy-ethyl methacrylate-methyl methacrylate, chitosan-carboxymethyl-cellulose, and alginate-polylysine-alginate.

9. A method of reducing the concentration of urea in a mammal comprising orally administering genetically engineered bacteria *Escherichia coli* DH5 which comprise the urease gene from *Klebsiella aerogens* in a pharmaceutically acceptable carrier, wherein the administration of said genetically engineered bacteria results in the removal of said urea from said mammal.

* * * * *